(12) United States Patent
Shimada

(10) Patent No.: US 12,114,881 B2
(45) Date of Patent: Oct. 15, 2024

(54) TREATMENT DEVICE

(71) Applicant: OLYMPUS CORPORATION, Hachioji (JP)

(72) Inventor: Ryuhei Shimada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 691 days.

(21) Appl. No.: 17/236,532

(22) Filed: Apr. 21, 2021

(65) Prior Publication Data
US 2021/0236153 A1 Aug. 5, 2021

Related U.S. Application Data

(63) Continuation of application No. PCT/JP2018/039245, filed on Oct. 22, 2018.

(51) Int. Cl.
*A61B 17/29* (2006.01)
*A61B 17/32* (2006.01)
*A61B 18/14* (2006.01)

(52) U.S. Cl.
CPC ...... *A61B 17/29* (2013.01); *A61B 17/320092* (2013.01); *A61B 18/1445* (2013.01); *A61B 2217/007* (2013.01)

(58) Field of Classification Search
CPC ............ A61B 17/29; A61B 17/320092; A61B 18/1445; A61B 2217/007; A61B 2017/320084; A61B 2017/320088
USPC ..................................... 606/45–52
See application file for complete search history.

(56) References Cited

U.S. PATENT DOCUMENTS

| | | | |
|---|---|---|---|
| 4,567,890 A * | 2/1986 | Ohta | A61B 18/1442 606/51 |
| 10,722,258 B2 * | 7/2020 | Batchelor | A61B 18/1445 |
| 2014/0194868 A1 * | 7/2014 | Sanai | A61B 18/1445 606/34 |
| 2014/0236140 A1 | 8/2014 | Honda et al. | |
| 2016/0143658 A1 * | 5/2016 | Stokes | A61B 17/320092 606/169 |
| 2017/0105790 A1 | 4/2017 | Onuma | |
| 2019/0117294 A1 | 4/2019 | Kano et al. | |

FOREIGN PATENT DOCUMENTS

| | | | |
|---|---|---|---|
| CN | 104135955 A | 11/2014 | |
| CN | 106535798 A | 3/2017 | |
| JP | S60-036041 A | 2/1985 | |
| JP | H08-294494 A | 11/1996 | |
| JP | 2005027809 A * | 2/2005 | ..... A61B 17/320092 |

(Continued)

OTHER PUBLICATIONS

Dec. 18, 2018 International Search Report issued in International Patent Application No. PCT/JP2018/039245.

(Continued)

*Primary Examiner* — Julian W Woo
*Assistant Examiner* — Osama Nemer
(74) *Attorney, Agent, or Firm* — Oliff PLC

(57) ABSTRACT

A treatment device includes: an end effector that includes a pair of grippers for gripping a target region; a channel for supplying a fluid to the end effector; and a fluid source for supplying the fluid to the channel. The treatment device is capable of controlling fluid flow to the end effector based on an open or closed state of the end effector.

13 Claims, 16 Drawing Sheets

(56) References Cited

FOREIGN PATENT DOCUMENTS

| | | |
|---|---|---|
| JP | 2009-240773 A | 10/2009 |
| WO | 2013/157571 A1 | 10/2013 |
| WO | 2013/187357 A1 | 12/2013 |
| WO | 2017/203635 A1 | 11/2017 |

OTHER PUBLICATIONS

Oct. 31, 2023 Office Action issued in Chinese Patent Application No. 201880098890.0.

* cited by examiner

TREATMENT DEVICE

CROSS-REFERENCE TO RELATED APPLICATION

This application is a continuation of International Application No. PCT/JP2018/039245, filed on Oct. 22, 2018, the entire contents of which are incorporated herein by reference.

BACKGROUND

1. Technical Field

The present disclosure relates to a treatment device.

2. Related Art

In the related art, there is a known treatment instrument provided with a unit that applies ultrasound energy (ultrasound vibrations) or high frequency energy (high frequency current) to biological tissue and that performs treatment (join (or, anastomose), and dissection, etc.) on the biological tissue by applying, for example, the ultrasound vibrations.

When treatment is performed on the biological tissue by using the treatment instrument, biological tissue sticks to a treatment portion due to burning of the tissue or the like. In order to suppress the sticking, a physiological saline solution can be supplied to the treatment portion immediately after energy is output in conjunction with the output of the energy.

SUMMARY

In some embodiments, a treatment device includes: an end effector that includes a pair of grippers for gripping a target region; a channel for supplying a fluid to the end effector; and a fluid source for supplying the fluid to the channel. The treatment device is capable of controlling fluid flow to the end effector based on an open or closed state of the end effector. For instance, the treatment device may include a clamp or projection or other mechanism for opening and closing the channel when the end effector is in a closed state and an open state, respectively.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
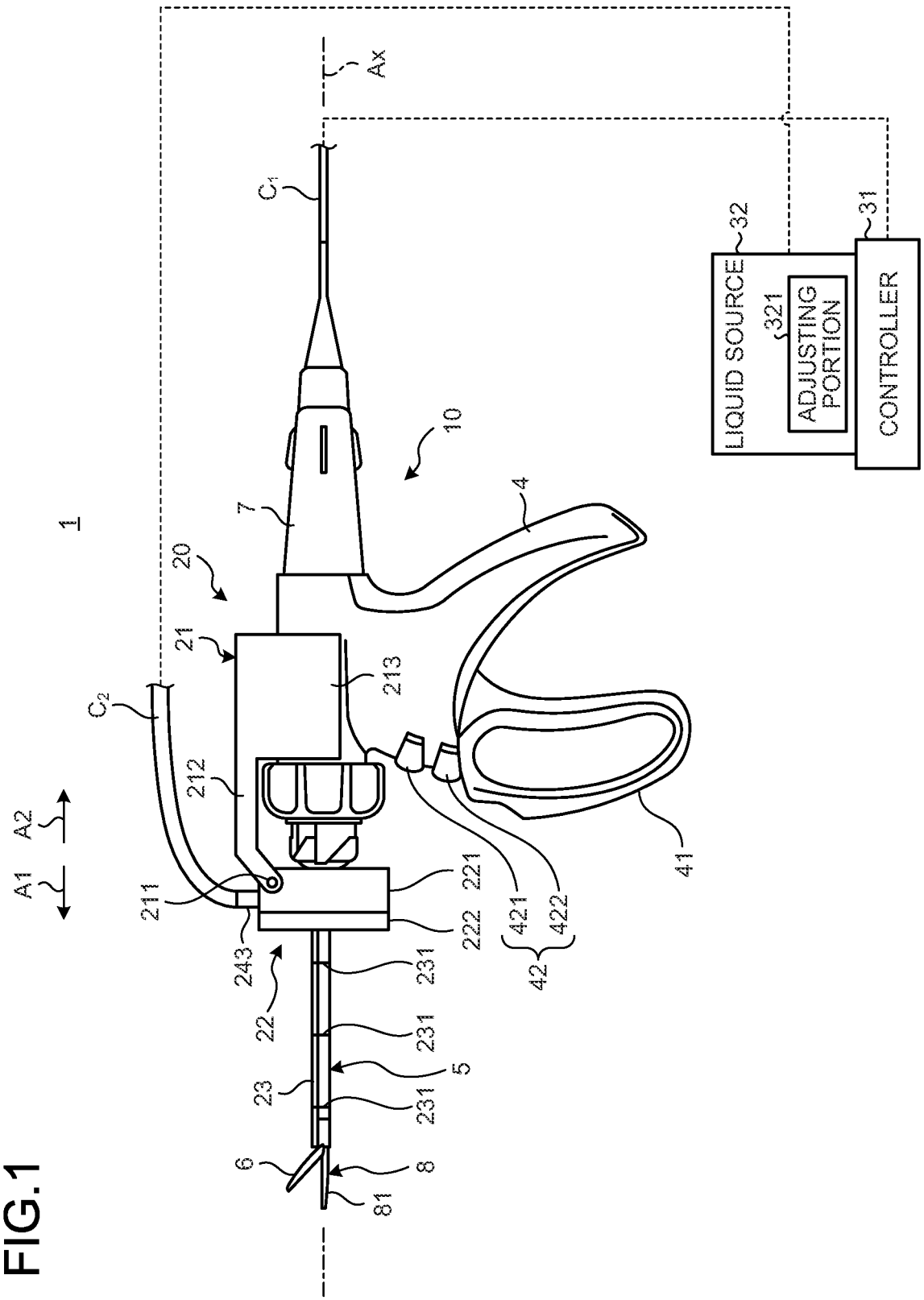
FIG. 1 is a diagram illustrating a treatment device according to an exemplary embodiment of the disclosure.

Preferred embodiments of a treatment instrument according to the disclosure will be explained with reference to accompanying drawings. Furthermore, the disclosure is not limited to these embodiments. Furthermore, in each of the drawings, components that are identical to those in embodiments are assigned the same reference numerals.

Figure 2:
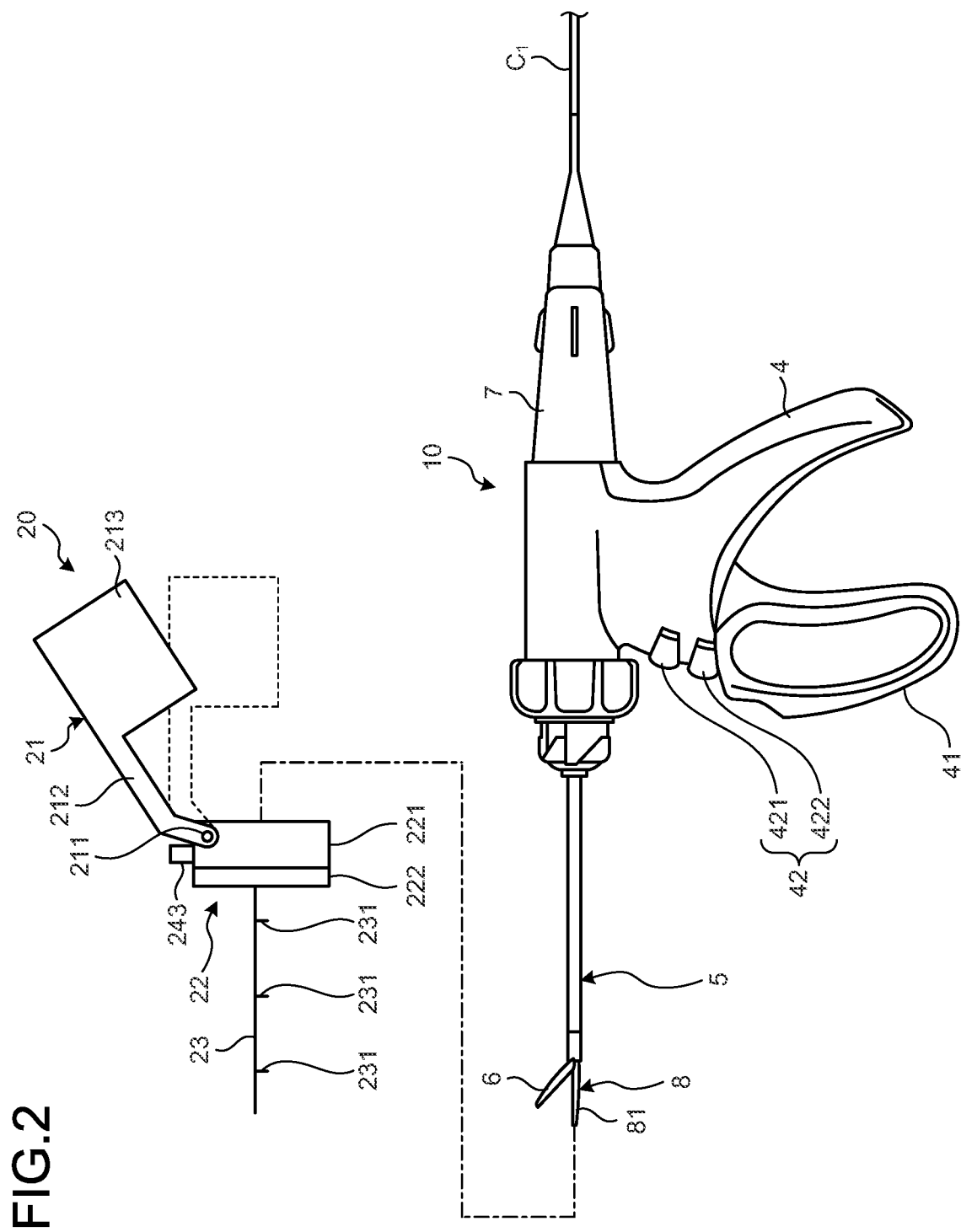
FIG. 2 is a diagram illustrating a configuration of the treatment device according to an exemplary embodiment of the disclosure in a case in which a liquid supply device is removed from the treatment instrument.

FIG. 1 is a schematic view illustrating a treatment device according to an embodiment of the disclosure. FIG. 2 is a diagram illustrating the treatment device according to the embodiment in a case in which a liquid supply device is removed from the treatment instrument. A treatment device 1 performs treatment on a region that targeted for the treatment of the biological tissue (hereinafter, referred to as a target region), by applying ultrasound energy or high frequency energy to the target region. Here, the treatment indicates, for example, solidification and incision of the target region. The treatment device 1 includes a treatment instrument 10, a liquid supply device 20, a controller 31, and a liquid source 32.

The treatment instrument 10 is a medical treatment instrument using, for example, a BLT (bolt-clamped Langevin-type transducer) for performing treatment on the target region through an abdominal wall. The treatment instrument 10 includes a handle 4, a sheath 5, a jaw 6, a transducer unit 7, and an ultrasound probe 8.

The handle 4 is a portion held by a hand of an operator. Furthermore, the handle 4 is provided with an operation knob 41 and an operation button 42. The operation button 42 is constituted by one or a plurality of switches (in the embodiment of FIGS. 1-8, two switches (switches 421 and 422)).

The sheath 5 has a cylindrical shape. Furthermore, in a description below, the central axis of the sheath 5 is referred to as the central axis Ax. Furthermore, in a description below, one of the sides of the central axis Ax is referred to as a distal end side A1 and the other side is referred to as a proximal end side A2. Then, the sheath 5 is attached to the handle 4 by inserting a part of the proximal end side A2 of the sheath 5 from the distal end side A1 of the handle 4 into the interior of the handle 4.

The jaw 6 is attached to the end portion of the distal end side A1 of the sheath 5 in a rotatable manner and grips the target region with the portion of the distal end side A1 of the ultrasound probe 8. Furthermore, an opening and closing mechanism that opens and closes, in accordance with the operation of the operation knob 41 performed by an operator, the jaw 6 with respect to the portion of the distal end side A1 of the ultrasound probe 8 is provided inside the handle 4 and the sheath 5 described above. The jaw 6 and the ultrasound probe 8 correspond to a gripper, and an end effector is formed by the jaw 6 and the ultrasound probe 8. The sheath 5 extends from the proximal end of the end effector toward the proximal end side A2.

The pad has insulation properties and prevents short circuits when high frequency energy is applied between the jaw 6 and the ultrasound probe 8. Furthermore, the pad can prevent damage of the ultrasound probe 8 caused by collision of the ultrasound probe 8 that is producing ultrasound vibrations with the jaw 6 when incision of the target region has been completed by the high frequency energy.

The liquid supply device 20 is attached to the outer circumference of the handle 4 and the sheath 5 so as to be freely inserted to and removed from the handle 4 and the sheath 5. The liquid supply device 20 includes a fixing portion 21 that is fixed to the handle 4, a coupling portion 22 that couples the interior of a main channel 23 to the interior of the liquid supply tube $C_2$ output from the liquid source 32, and the main channel 23 that is projected along the outer side of the sheath 5. The liquid supply device 20 will be described in detail later.

The controller 31 is electrically connected to the treatment instrument 10 by an electric cable $C_1$ and performs overall control of an operation of the treatment instrument 10. Furthermore, the controller 31 controls a supply of a physiological saline solution from the liquid source 32. The controller 31 is, for example, a central processing unit (CPU), a field-programmable gate array (FPGA), or the like and controls a supply of a high frequency current and ultrasound vibrations in accordance with a predetermined control program when the operation button 42 is pressed by an operator. The controller 31 corresponds to a liquid supply control mechanism.

The liquid source 32 supplies a liquid, such as a physiological saline solution, to the liquid supply device 20. In the liquid source 32, the flow rated of the physiological saline solution per unit of time flowing toward the liquid supply device 20 is adjusted under the control of the controller 31. The liquid source 32 is accommodated in, for example, a transportation bag. Furthermore, the liquid source 32 includes an adjusting portion 321 formed by a valve or the like attached to the transportation bag. In the adjusting portion 321, for example, a valve opens and closes under the control of the controller 31. Furthermore, a fluid may also be supplied from the liquid source 32 to the liquid supply device 20 by a pump that is not illustrated. Alternatively, the fluid may also be supplied to the liquid supply device 20 due to gravity by arranging the liquid source 32 at the position higher than the liquid supply device 20. The liquid source 32 corresponds to a fluid source.

Figure 3:
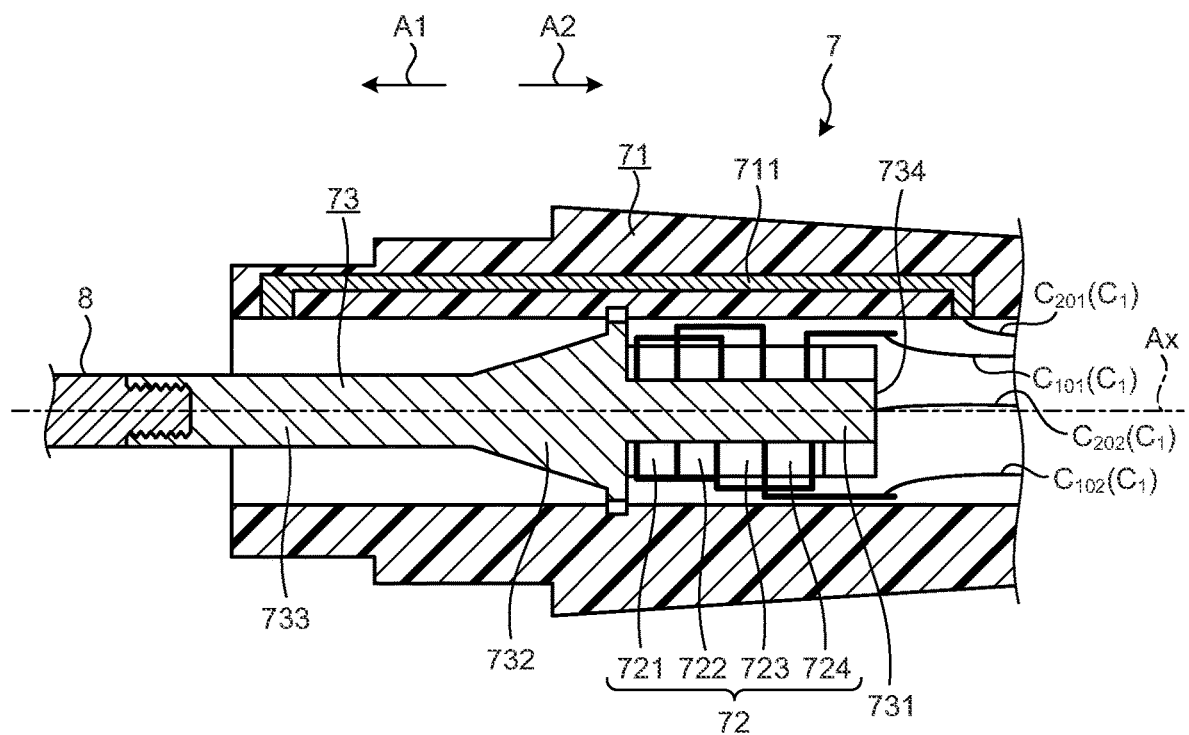
FIG. 3 is a sectional view illustrating a transducer unit in the treatment instrument according to an exemplary embodiment of the disclosure.

FIG. 3 is a sectional view illustrating the transducer unit 7. Specifically, FIG. 3 is a sectional view obtained by cutting the transducer unit 7 by a plane including the central axis Ax. The transducer unit 7 includes, as illustrated in FIG. 3, a transducer case 71, an ultrasound transducer 72, and a horn 73.

The transducer case 71 extends linearly along the central axis Ax and is attached to the handle 4 by inserting a part of the distal end side A1 of the transducer case 71 from the proximal end side A2 of the handle 4 into the inside of the handle 4. Then, in the state in which the transducer case 71 is attached to the handle 4, the end portion of the distal end side A1 thereof is coupled to the end portion of the proximal end side A2 of the sheath 5.

The ultrasound transducer 72 is accommodated inside the transducer case 71 and ultrasound vibrations are generated under the control of the controller 31. In the embodiment, the ultrasound vibration is a longitudinal vibration that vibrates in the direction along the central axis Ax. The ultrasound transducer 72 is a BLT provided with a plurality of piezoelectric elements 721 to 724 layered along the central axis Ax (see FIG. 3). Furthermore, in the embodiment, four of the piezoelectric elements 721 to 724 are provided; however, the number of piezoelectric elements is not limited to four and the other number of piezoelectric elements may also be provided.

The horn 73 is accommodated inside the transducer case 71 and expands the amplitude of the ultrasound vibration generated by the ultrasound transducer 72. The horn 73 has a long shape extending linearly along the central axis Ax. Furthermore, the horn 73 includes, from the proximal end side A2 toward the distal end side A1, a transducer mounting portion 731 on which the ultrasound transducer 72 is mounted, a sectional area changing portion 732 that has a tapered shape in the cross-sectional area toward the distal end side A1 and that expands the amplitude of the ultrasound vibration, and a probe mounting portion 733 on which the ultrasound probe 8 is mounted (see FIG. 3).

The ultrasound probe 8 has a long shape extending linearly along the central axis Ax and is inserted into inside the sheath 5 in a state in which the portion of the distal end side A1 externally protrudes. Furthermore, the end portion of the proximal end side A2 of the ultrasound probe 8 is connected to the probe mounting portion 733. In contrast, at the end portion of the distal end side A1 of the ultrasound probe 8, a treatment portion 81 that grips the target region with the jaw 6 and performs treatment is provided. Then, the ultrasound probe 8 performs treatment on the target region by transmitting the ultrasound vibration generated by the ultrasound transducer 72 from the end portion of the proximal end side A2 to the end portion (the treatment portion 81) of the distal end side A1 via the horn 73 and applying the ultrasound vibration to the target region from the treatment portion 81.

Here, a pair of transducer purpose lead wires $C_{101}$ and $C_{102}$ constituting an electric cable $C_1$ is joined to the ultrasound transducer 72 (see FIG. 3).

Then, the controller 31 supplies alternating-current power to the ultrasound transducer 72 via the pair of the transducer purpose lead wires $C_{101}$ and $C_{102}$. Accordingly, the ultrasound transducer 72 generates ultrasound vibrations.

Here, the transducer case 71 is provided with a first conductive portion 711 that extends from the end portion of the proximal end side A2 toward the end portion of the distal end side A1 (see FIG. 3). Furthermore, although a specific illustration has been omitted, the sheath 5 is provided with a second conductive portion that extends from the end portion of the proximal end side A2 toward the end portion of the distal end side A1 and that electrically connects the first conductive portion 711 and the jaw 6. Furthermore, at the end portion of the proximal end side A2 of the first conductive portion 711, a high frequency purpose lead wire $C_{201}$ constituting the electric cable $C_1$ is joined. Furthermore, at the end portion (an end portion 734) of the transducer mounting portion 731, a high frequency purpose lead wire $C_{202}$ constituting the electric cable $C_1$ is joined.

Then, the controller 31 supplies a high frequency current between the jaw 6 and the ultrasound probe 8 via the pair of the high frequency purpose lead wire $C_{201}$ and $C_{202}$, the first conductive portion 711, the second conductive portion, and the horn 73. Accordingly, the high frequency current flows the target region that is gripped between the jaw 6 and the portion of the distal end side A1 of the ultrasound probe 8. Namely, the jaw 6 and the ultrasound probe 8 also function as a high frequency electrode. In other words, the treatment instrument 10 also functions as a bipolar treatment instrument by both of the jaw 6 and the ultrasound probe 8 functioning as a pair of high frequency electrodes.

Figure 4:
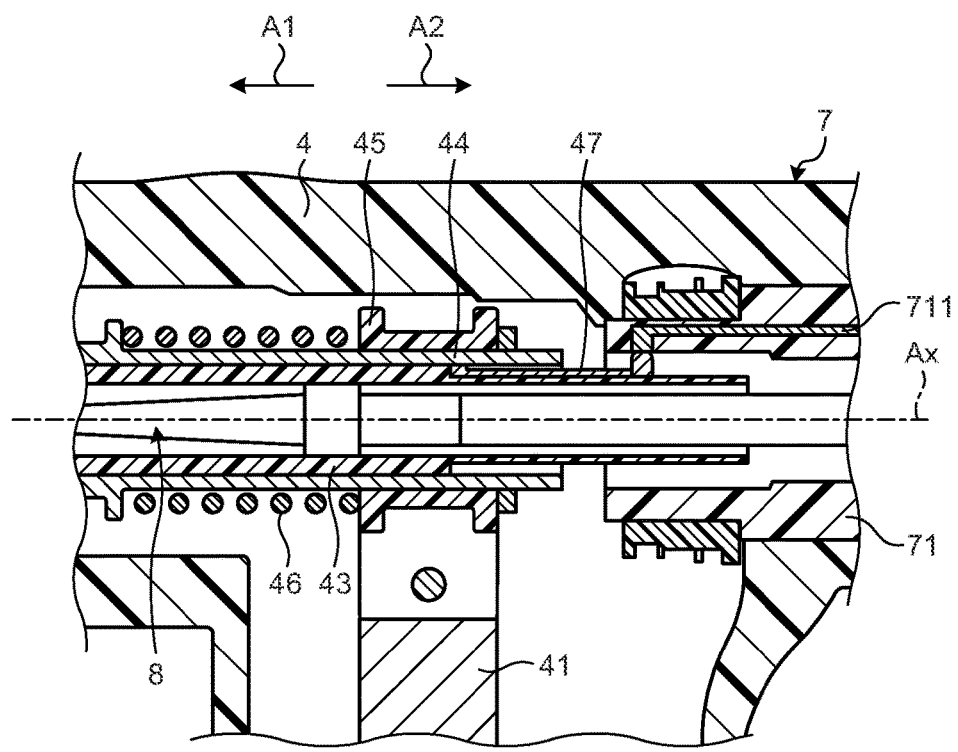
FIG. 4 is a sectional view illustrating an internal configuration of a handle in the treatment instrument according to an exemplary embodiment of the disclosure.

FIG. 4 is a diagram illustrating an internal configuration of the handle 4. A connecting cylindrical portion 43 formed of an insulating material (nonconductive material) and a movable cylindrical portion 44 provided on an outer circumferential direction side of the connecting cylindrical portion 43 are provided in the interior of the handle 4.

The movable cylindrical portion 44 is formed of a conductive material and can move along the longitudinal axis Ax with respect to the transducer case 71 and the connecting cylindrical portion 43. A sliding member 45 formed of an insulating material (nonconductive material) is provided on the outer circumferential portion of the movable cylindrical portion 44.

The sliding member 45 can move along the longitudinal axis Ax with respect to the movable cylindrical portion 44. An elastic member 46 is provided between the sliding member 45 and the movable cylindrical portion 44. The elastic member 46 is constituted by a coil spring or the like.

Furthermore, an operation knob 41 is attached to the sliding member 45. By opening and closing the operation knob 41 with respect to the handle 4, a driving force is transmitted to the sliding member 45, and thus, the sliding member 45 moves along the longitudinal axis Ax. Then, the driving force is transmitted from the sliding member 45 to the movable cylindrical portion 44 via the elastic member 46 and the movable cylindrical portion 44 moves along the longitudinal axis Ax with respect to the transducer case 71 and the connecting cylindrical portion 43.

Furthermore, a plate shaped contact member 47 formed of a conductive material is fixed to the connecting cylindrical portion 43. In a state in which the transducer case 71 is connected to the handle 4, an end of the contact member 47 abuts against the first conductive portion 711 of the transducer case 71 and the movable cylindrical portion 44 movably abuts against the other end of the contact member 47. Accordingly, in the state in which the transducer case 71 is connected to the handle 4, the first conductive portion 711 in the transducer case 71 and the movable cylindrical portion 44 are electrically connected via the contact member 47. Accordingly, high frequency energy is supplied (transmitted) from the controller 31 to the movable cylindrical portion 44 of the sheath 5 passing through the first conductive portion 711 in the transducer case 71. Furthermore, the first conductive portion 711 in the transducer case 71 and the movable cylindrical portion 44 of the sheath 5 are electrically insulated with respect to the horn 73 and the ultrasound probe 8.

A switch (not illustrated) is provided inside the handle 4. The switch is closed by pressing the operation button 42 and by inputting an energy operation. The switch is electrically connected to the controller 31. An electrical signal is transmitted to the controller 31 by closing the switch and an input of the energy operation is detected. For example, because the input of the energy operation is detected by pressing an operation button 421, ultrasound energy and high frequency energy are output from the controller 31, and, by pressing an operation button 422, high frequency energy (or ultrasound energy) is output from the controller 31.

Figure 5:
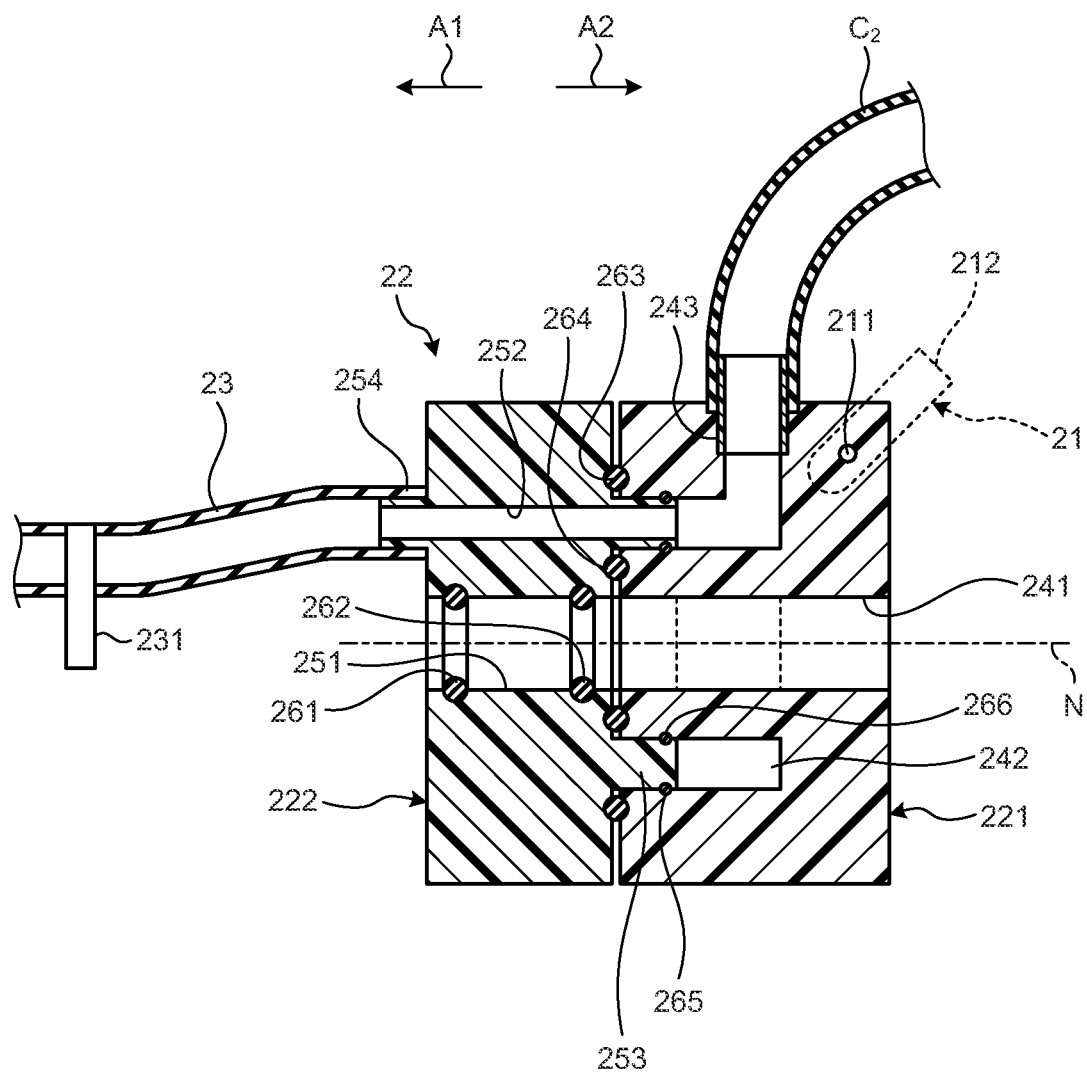
FIG. 5 is a sectional view illustrating a liquid supply device in the treatment device according to an exemplary embodiment of the disclosure.

The liquid supply device 20 is attached to the outer circumferences of the handle 4 and the sheath 5 so as to be freely inserted to and removed from the handle 4 and the sheath 5. The liquid supply device 20 includes the fixing portion 21 that is fixed to the handle 4, the coupling portion 22 that couples the interior of the main channel 23 to the interior of the liquid supply tube $C_2$ from the liquid source 32, and the main channel 23 extending along an outer side of the sheath 5. FIG. 5 is a sectional view illustrating the liquid supply device in the treatment device according to the present embodiment of the disclosure.

The fixing portion 21 has a rotatable hinge portion 211 with respect to the coupling portion 22. The fixing portion 21 rotates between the position indicated by the solid line and the position indicated by a broken line by the hinge portion 211 (see FIG. 2).

Furthermore, the fixing portion 21 is pivotally supported by the hinge portion 211 of the coupling portion 22 and has a rotatable arm 212 and a holding portion 213 that is held by the handle 4. The holding portion 213 functions as a grasping portion that grasps the handle 4.

The coupling portion 22 has a fixed adapter 221 and a rotating adapter 222. A description will be given with the assumption that the external shape of the fixed adapter 221 and the rotating adapter 222 is a circular shape; however, an appropriate shape is allowed.

The fixed adapter 221 has a through hole 241 passing through along the central axis N of the main body of the fixed adapter 221 and an annular channel 242 formed concentrically with respect to the central axis N. The annular channel 242 is formed from the distal end side A1 of the main body of the fixed adapter 221 toward the proximal end side A2, but does not reach the surface of the proximal end side A2. A connector 243 communicating with the annular channel 242 is disposed at the fixed adapter 221. The central axis N is aligned with the central axis Ax when the liquid supply device 20 is mounted on the treatment instrument 10.

The fixed adapter 221 is coupled to the fixing portion 21. Accordingly, when a fixing portion 21 is fixed to the handle 4, the fixed adapter 221 maintains the positioning state with respect to the handle 4.

The opening diameter of the through hole 241 is formed so as to be slightly greater than the outer diameter of the sheath 5. When the fixing portion 21 is fixed to the handle 4, the sheath 5 and the ultrasound probe 8 is freely rotatable inside the through hole 241 of the fixed adapter 221.

The rotating adapter 222 is rotatable about the axis of the central axis N with respect to the fixed adapter 221. The rotating adapter 222 has a through hole 251, a channel 252, and an annular convex portion 253.

The through hole 251 passes along the central axis N.

The channel 252 is formed parallel to the central axis N.

The annular convex portion 253 protrudes in the direction orthogonal to the central axis N.

The opening diameter of the through hole 251 is formed so as to be slightly greater than the outer diameter of the sheath 5. Sealing members 261 and 262, such asC O ring is disposed on the inner circumferential surface of the through hole 251. The sheath 5 is supported by the sealing members 261 and 262 inside the through hole 251 of the rotating adapter 222. Accordingly, the rotating adapter 222 rotates according to the rotation of the sheath 5 and the ultrasound probe 8.

Furthermore, it is preferable that O rings 263 and 264 are disposed between the surface of the distal end side A1 of the fixed adapter 221 and the surface of the proximal end side A2 of the rotating adapter 222. Furthermore, it is also preferable that O rings 265 and 266 are disposed between the inner circumferential surface and the outer circumferential surface of the annular convex portion 253 and the annular channel 242.

The annular convex portion 253 can be fitted into the annular channel 242 of the fixed adapter 221. The channel 252 passes between the surface of the proximal end side A2 of the coupling portion 22 (the annular convex portion 253) and the surface of the distal end side A1 of the coupling portion 22.

A connector 254 communicating with the channel 252 is formed on the distal end surface of the rotating adapter 222. The proximal end of the main channel 23 is coupled to the connector 254. The distal end of the main channel 23 is opened in the vicinity of the distal end of the sheath 5. Namely, an opening 230 of the distal end side of the main channel 23 is located in the vicinity of the distal end of the sheath 5. In the present embodiment, the opening of the distal end of the main channel 23 is disposed at the position at which a fluid is supplied to the end effector, specifically, at the proximal end side of the jaw 6 that will be described later.

On the main channel 23, for example, pinch bodies 231 that have a C shape and are capable of elastic deformation are arranged at appropriate intervals. The pinch bodies 231 are elastically deformed and hold the outer circumferential surface of the sheath 5.

Figure 6:
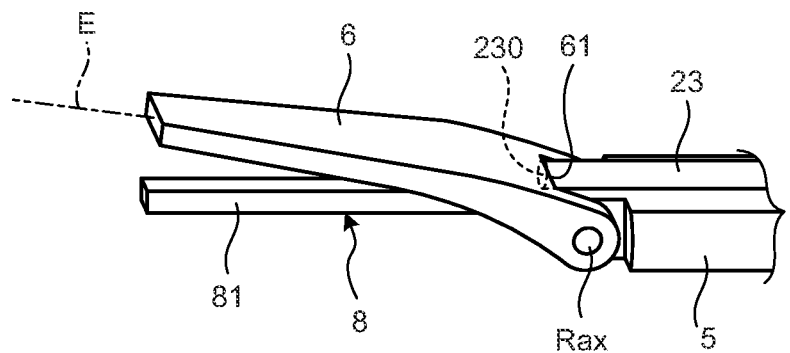
FIG. 6 is a diagram illustrating a distal end portion of the treatment instrument in the treatment device according to an exemplary embodiment of the disclosure.
Figure 7:
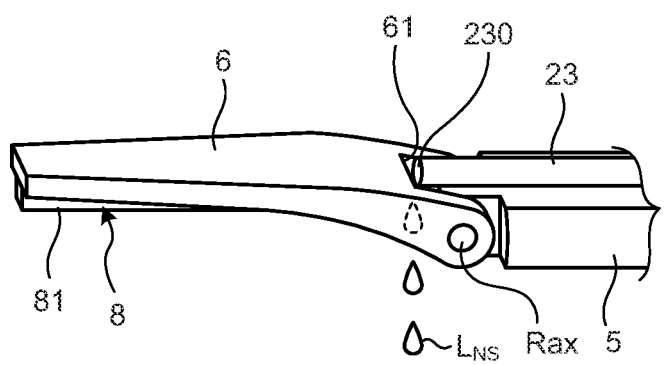
FIG. 7 is a diagram illustrating a distal end portion of the treatment instrument in the treatment device according to an exemplary embodiment of the disclosure.

FIG. 6 and FIG. 7 are diagrams each illustrating the distal end portion of the treatment instrument in the treatment device according to the present embodiment of the disclosure. FIG. 6 indicates an open state in which the jaw 6 is away from the ultrasound probe 8. FIG. 7 indicates a closed state in which the jaw 6 approaches and is in contact with the ultrasound probe 8.

The jaw 6 extends along the extending axis (jaw axis) E from the proximal end direction toward the distal end direction. The extending axis E is the central axis of the jaw 6 and, in the state in which the jaw 6 is closed with respect to the ultrasound probe 8 (see FIG. 7), the extending axis E of the jaw 6 is substantially parallel to the longitudinal axis Ax (see FIG. 1). One of the directions perpendicular to the longitudinal axis Ax and the extending axis E is an opening direction of the jaw 6 and the opposite direction of the opening direction is a closing direction of the jaw 6. The jaw 6 rotates about the rotation axis Rax provided on the proximal end side of the jaw 6. Here, it is preferable that the opening 230 of the main channel 23 is located closer to the distal end side A1 than the rotation axis Rax. With this arrangement, it is possible to further accurately supply the physiological saline solution discharged from the opening 230 to the end effector and the target region.

Furthermore, a hole 61 into which the main channel 23 can be inserted is formed in the jaw 6. The hole 61 is a hole for allowing the physiological saline solution output from, for example, the main channel 23 to flow from the distal end of the jaw 6 or the central portion of the jaw 6 toward the target region.

Here, the treatment portion 81 (longitudinal axis Ax) may also be bent toward a first width direction at the distal end of the ultrasound probe 8. By bending the distal end of the treatment portion 81, visibility of an operator is improved at the time of treatment. Furthermore, at this time, in also the jaw 6, the jaw 6 (extending axis E) is bent toward the first width direction in accordance with the bending state of the ultrasound probe 8. By also allowing the jaw 6 to be bent, the jaw 6 extends in a state facing the ultrasound probe 8 (the treatment portion 81).

A weak current is supplied to the jaw 6 and the ultrasound probe 8 from the controller 31 via the cable $C_1$ or the like. Accordingly, when the jaw 6 and the ultrasound probe 8 contact with each other, or, when the target region is grasped by the jaw 6 and the ultrasound probe 8, electrical continuity occurs between the jaw 6 and the ultrasound probe 8. The impedance detected by the controller 31 is changed due to the electrical continuity. Furthermore, the intensity of the current (weak current) flowing here is low enough that does not affect a human body.

The controller 31 detects a change in impedance between the jaw 6 and the ultrasound probe 8 and controls the adjusting portion 321 (valve) of the liquid source 32 in accordance with the detection result. Specifically, the controller 31 periodically detects the impedance and opens the valve when an amount of temporal change in impedance is greater than a threshold. In the present embodiment, if the jaw 6 and the ultrasound probe 8 are in the closed state or if the jaw 6 and the ultrasound probe 8 grip the target region, the physiological saline solution is supplied to the end effector and the target region.

After that, the controller 31 controls, based on an input of the energy operation triggered when the operation button 42 is pressed, an output of the ultrasound energy or an output of the high frequency energy. At this time, before the ultrasound energy or the high frequency energy is output, the end effector and the target region are in a wet state due to the physiological saline solution.

In the following, an example of an operation of the treatment device 1 described above will be described. The operator holds the treatment instrument 10 by the operator's hand and inserts the distal end portion of the treatment instrument 10 into the abdominal cavity via the abdominal wall by using, for example, a trocar or the like.

Figure 8:
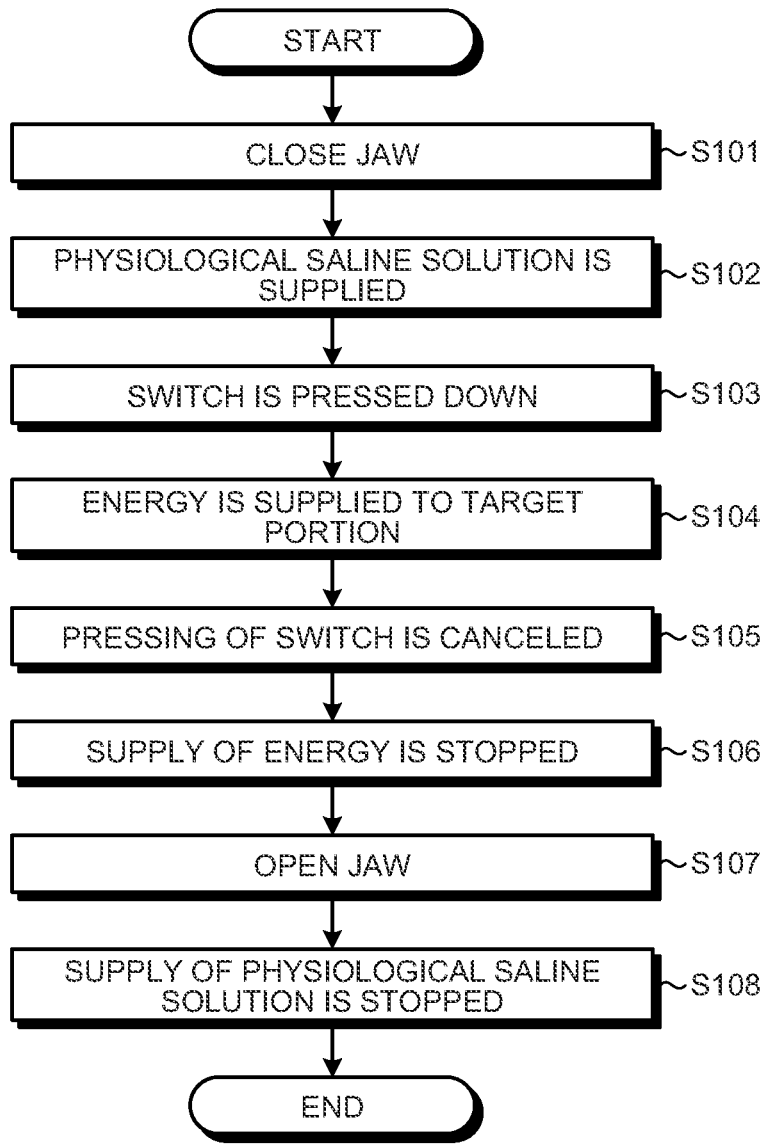
FIG. 8 is a flowchart illustrating treatment performed by the treatment device according to an exemplary embodiment of the disclosure.

After that, the operator performs treatment on the target region by using the treatment device 1. FIG. 8 is a flowchart illustrating the treatment performed by the treatment device according to the present embodiment of the disclosure. The operator operates the operation knob 41 and closes the jaw 6 with respect to a treatment portion 81, thereby gripping the target region by the jaw 6 and the treatment portion 81 (Step S101). At this time, the controller 31 detects a change in impedance and starts a supply of the physiological saline solution (Step S102). Under the control of the controller 31, the physiological saline solution supplied from the liquid source 32 is supplied to the end effector and the target region via the tube $C_2$ and the liquid supply device 20.

After that, the operator presses the operation button 42 (Step S103).

Then, the controller 31 performs energy supply control described below (Step S104).

When, for example, the operation button 421 is pressed, the controller 31 supplies a high frequency current between the jaw 6 and the ultrasound probe 8 via the pair of the high frequency purpose lead wires $C_{201}$ and $C_{202}$, the first conductive portion 711, the second conductive portion, and the horn 73. Furthermore, at substantially the same time as the supply of the high frequency current between the jaw 6 and the ultrasound probe 8, the controller 31 supplies alternating-current power to the ultrasound transducer 72 via the pair of the transducer purpose lead wires $C_{101}$ and $C_{102}$, thereby allowing the ultrasound transducer 72 to generate ultrasound vibrations. Namely, Joule heat is generated in the target region due to the flow of the high frequency current. Furthermore, friction heat is generated between the instrument surface and the target region due to longitudinal vibrations of the treatment portion 81. Then, the target region is subjected to incision while being solidified.

Furthermore, an atmospheric pressure fluctuation is generated due to ultrasound vibrations. Air bubbles in the physiological saline solution is ruptured due to the atmospheric pressure fluctuation, whereby a shock wave is generated. Then, the shock wave removes a stain in the target region or assists an incision process.

After that, the operator cancels the operation button 42 that is pressed (Step S105). When the operation button 42 that is pressed is cancelled, the controller 31 stops the supply of energy (Step S106).

After stopping the supply of the energy, the operator operates the operation knob 41 and cancels the gripping state of the target region by opening the jaw 6 with respect to the treatment portion 81 (Step S107).

When the jaw 6 is opened by an operation of the operation knob 41, the controller 31 detects a change in impedance, and then, the supply of the physiological saline solution is stopped (Step S108).

In the present embodiment described above, a supply of the physiological saline solution is controlled based on a change in impedance in accordance with an opening and closing operation of the jaw 6 with respect to the ultrasound probe 8. Specifically, if the jaw 6 and the ultrasound probe 8 are in the closed state or if the jaw 6 and the ultrasound probe 8 grip the target region, the physiological saline solution is supplied to the end effector. According to the present embodiment, because the physiological saline solution is supplied to the target region without pressing the operation button, it is possible to improve the operability related to the supply of the physiological saline solution to the treatment portion of the treatment instrument.

Furthermore, in the present embodiment described above, because the physiological saline solution is supplied to the target region before energy is applied, it is possible to prevent the target region solidified or dried due to the applied energy from being attached to the jaw 6 or the ultrasound probe 8.

Furthermore, in the present embodiment described above, a description has been given with the assumption that a supply of the physiological saline solution is controlled by detecting a change in impedance between the jaw 6 and the ultrasound probe 8; however, it may also be possible to control the supply of the physiological saline solution based on a change in weak current flowing between the jaw 6 and the ultrasound probe 8.

Figure 9:
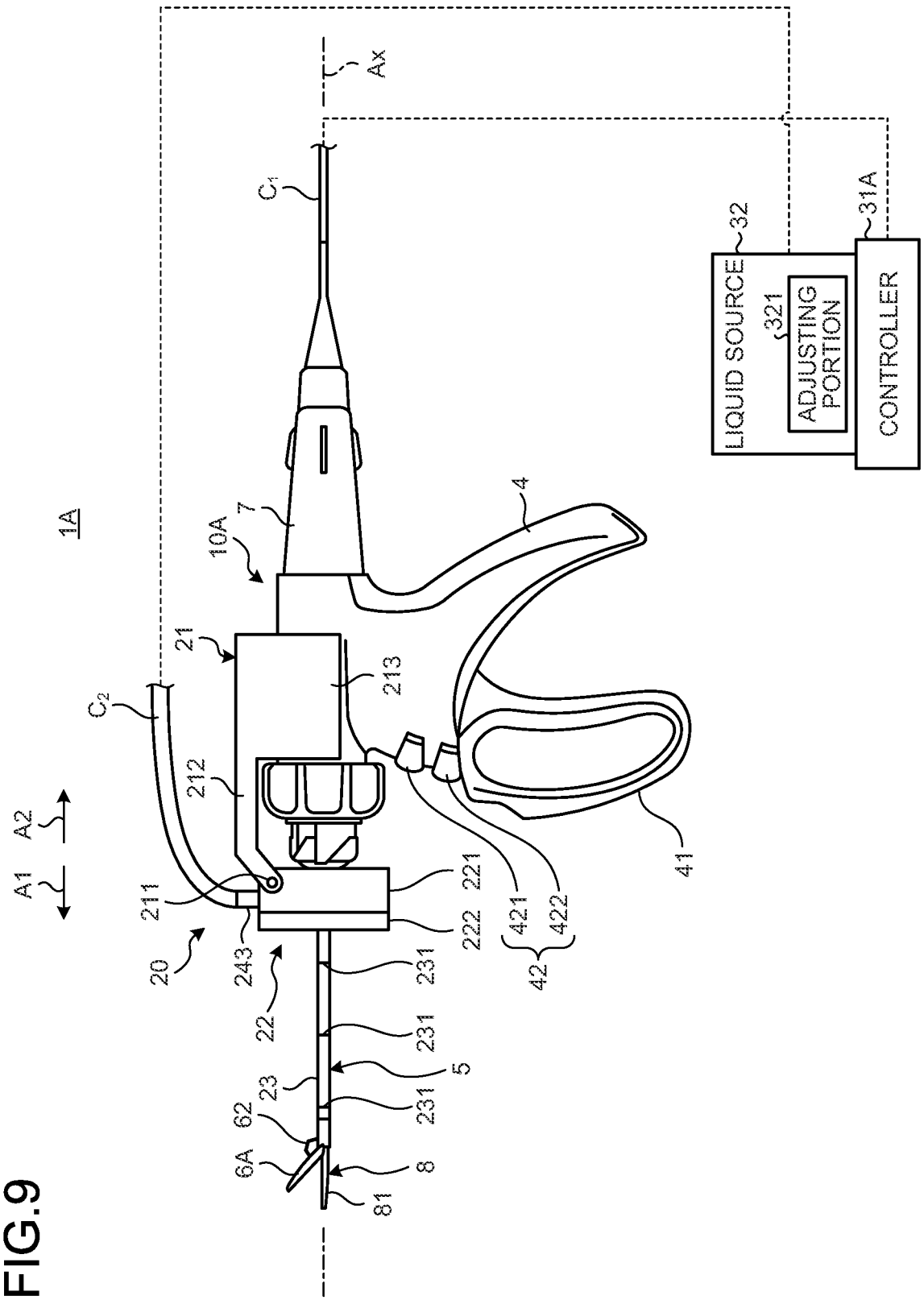
FIG. 9 is a diagram illustrating a treatment device according to an exemplary embodiment of the disclosure.

FIG. 9 is a diagram illustrating a treatment device according to another exemplary embodiment of the disclosure. A treatment device 1A illustrated in the drawing performs treatment on the target region by applying ultrasound energy or high frequency energy to the target region. The treatment device 1A includes a treatment instrument 10A, the liquid supply device 20, a controller 31A, and the liquid source 32. The treatment device 1A according to the present embodiment has the same configuration as that described in the above embodiment except that the treatment instrument 10 in the treatment device 1 described above is replaced with the treatment instrument 10A and the controller 31 is replaced with the controller 31A. In the following, the treatment instrument 10A and the controller 31A each having a configuration different from that described in the above embodiment will be described.

Similarly to the treatment instrument 10, the treatment instrument 10A is a medical treatment instrument that uses the BLT for performing treatment on the target region. The treatment instrument 10A includes the handle 4, the sheath 5, a jaw 6A, the transducer unit 7, and the ultrasound probe 8. In the following, the jaw 6A having a configuration different from that in the above described embodiment of FIGS. 1-8 will be described.

The jaw 6A is attached to the end portion of the distal end side A1 of the sheath 5 in a rotatable manner and grips the target region with the portion of the distal end side A1 of the ultrasound probe 8. Furthermore, in the interior of each of the handle 4 and the sheath 5 described above, an opening and closing mechanism that opens and closes the jaw 6A with respect to the portion of the distal end side A1 of the ultrasound probe 8 in accordance with the operation knob 41 operated by an operator is provided. An end effector is constituted by the jaw 6A and the ultrasound probe 8. Furthermore, the hole 61 into which the main channel 23 be inserted is provided in the jaw 6A.

In the jaw 6A, a clamp 62 is provided on the opposite side of the ultrasound probe 8. When the jaw 6A is in an open state, the clamp 62 crushes and seals the main channel 23. At this time, the clamp 62 sandwiches and blocks the main channel 23 with the sheath 5. In contrast, when the jaw 6A is in a closed state, a contact state of the clamp 62 with respect to the main channel 23 is cancelled.

The controller 31A is electrically connected to the treatment instrument 10 by the electric cable $C_1$ and performs overall control of the operation of the treatment instrument 10. Furthermore, the controller 31A controls a supply of the physiological saline solution from the liquid source 32. The controller 31A is, for example, a CPU, an FPGA, or the like and controls, when the operation button 42 is pressed by an operator, a supply of a high frequency current or a ultrasound vibration in accordance with a predetermined control program. In the present embodiment, the controller 31A controls a supply of the physiological saline solution at a predetermined set flow rate with respect to the liquid source 32.

In the present embodiment, the controller 31A and the clamp 62 correspond to a liquid supply control mechanism. Furthermore, in a case of configuration in which a liquid is supplied from the liquid source 32 to the liquid supply device 20 by gravity, only the clamp 62 constitutes the liquid supply control mechanism.

Figure 10:
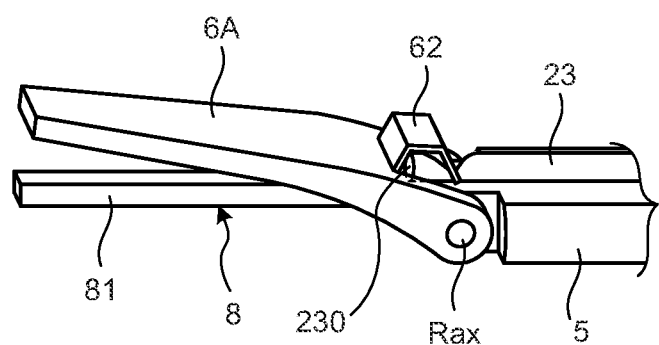
FIG. 10 is a diagram illustrating a distal end portion of a treatment instrument in the treatment device according to an exemplary embodiment of the disclosure.
Figure 11:
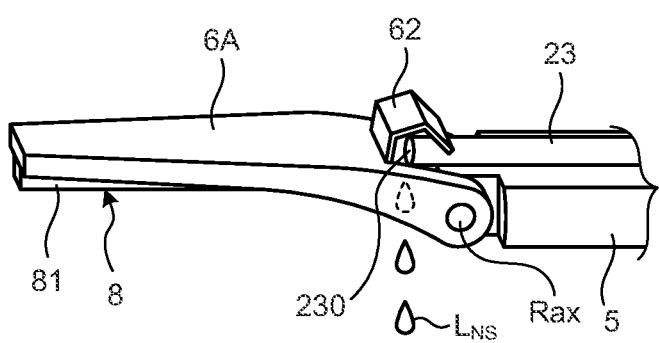
FIG. 11 is a diagram illustrating the distal end portion of the treatment instrument in the treatment device according to an exemplary embodiment of the disclosure.

FIG. 10 and FIG. 11 are diagrams each illustrating the distal end portion of the treatment instrument in the treatment device according to the present embodiment of the disclosure. FIG. 10 indicates an open state in which the jaw 6A is away from the ultrasound probe 8. FIG. 11 indicates a closed state in which the jaw 6A approaches and is in contact with the ultrasound probe 8.

In the open state in which the jaw 6A and the ultrasound probe 8 are separated, because the clamp 62 is in a state in which the clamp 62 crushes the main channel 23 with the sheath 5 (see FIG. 10), the physiological saline solution is not discharged from the main channel 23. In contrast, in the closed state in which the jaw 6A is in contact with the ultrasound probe 8 or the jaw 6A grips the target region, because the contact between the clamp 62 and the main channel 23 is cancelled (see FIG. 11), the physiological saline solution is discharged from the opening 230 of the main channel 23. Here, similarly to the embodiment of FIGS. 1-8, it is preferable that the opening 230 is disposed closer to the distal end side than the rotation axis Rax of the jaw 6A. With this arrangement, it is possible to further accurately supply the physiological saline solution discharged from the opening 230 due to opening and closing of the jaw 6A to the end effector and the target region. In this embodiment, if the jaw 6A and the ultrasound probe 8 are in the closed state or if the jaw 6A and the ultrasound probe 8 grip the target region, the physiological saline solution is supplied to the end effector and the target region.

In the embodiment described above, the supply of the physiological saline solution is controlled by changing the contact mode between the clamp 62 and the main channel 23 in accordance with the opening and closing operation of the jaw 6A performed with respect to the ultrasound probe 8. Specifically, if the jaw 6A and the ultrasound probe 8 are in the closed state or if the jaw 6A and the ultrasound probe 8 grip the target region, the physiological saline solution is supplied to the end effector. According to this embodiment, because the physiological saline solution is supplied to the target region without pressing the operation button, it is possible to improve the operability related to the supply of the physiological saline solution to the treatment portion of the treatment instrument.

Furthermore, in the embodiment described above, because the configuration is structured such that the supply is stopped by the clamp 62 crushing the main channel 23, it is possible to control the supply of the physiological saline solution with a simple configuration.

Furthermore, in the embodiment described above, similarly to the embodiment described above (e.g., FIGS. 1-8), because the physiological saline solution is supplied to the target region before energy is applied, it is possible to prevent the target region solidified or dried due to the applied energy from being attached to the jaw 6A or the ultrasound probe 8.

Figure 12:
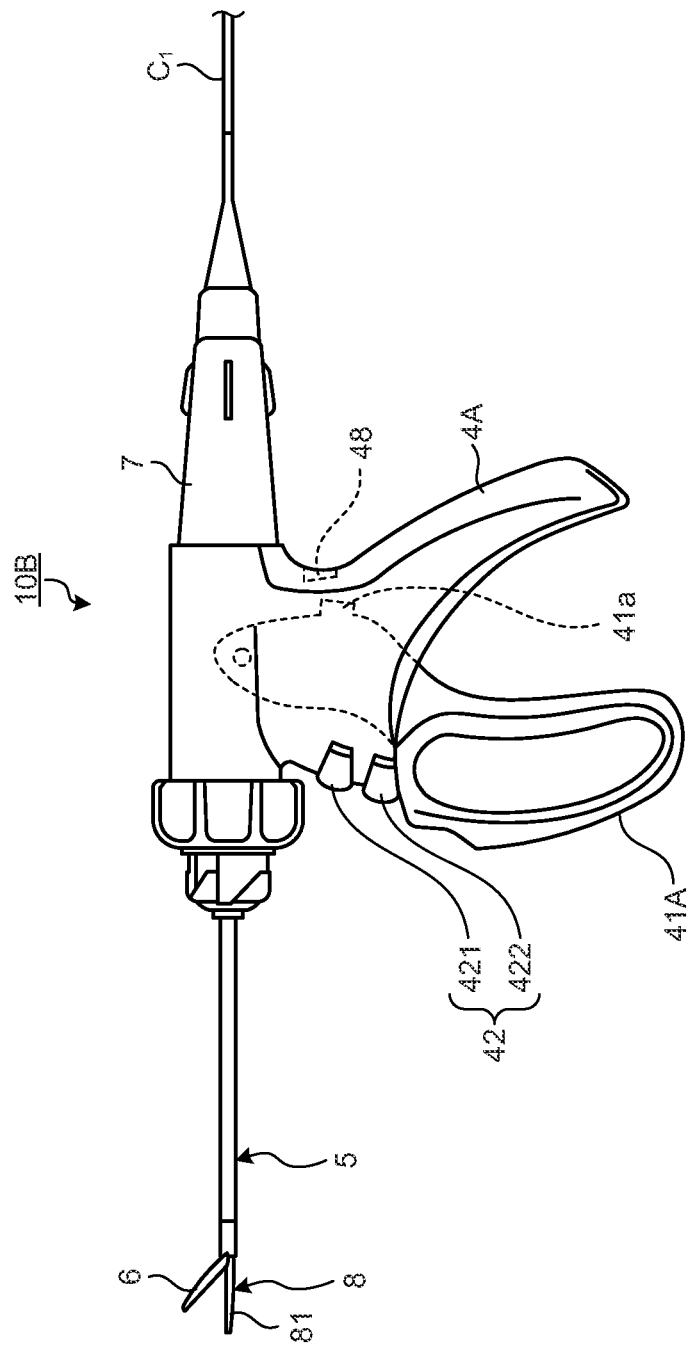
FIG. 12 is a diagram illustrating a treatment instrument in a treatment device according to an exemplary embodiment of the disclosure.
Figure 13:
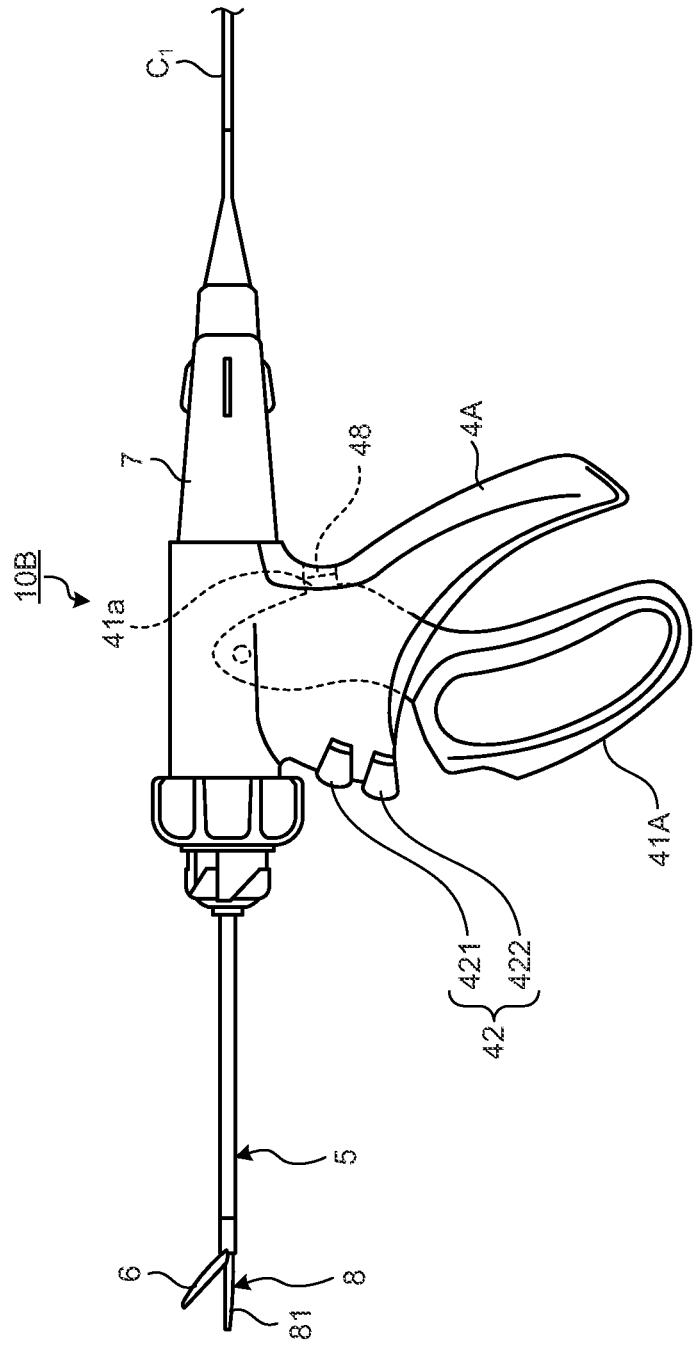
FIG. 13 is a diagram illustrating the treatment instrument in the treatment device according to an exemplary embodiment of the disclosure.

FIG. 12 and FIG. 13 are diagrams each illustrating a treatment instrument in a treatment device according to another exemplary embodiment of the disclosure. The treatment device illustrated in the drawings performs treatment on a target region by applying ultrasound energy or high frequency energy to the target region. The treatment device has the same configuration as that of the treatment device 1 except that the treatment instrument 10 in the treatment device 1 described above is replaced with a treatment instrument 10B. In the following, the treatment instrument 10B having a configuration different from that described in the embodiment of FIGS. 1-8 will be described.

Similarly to the treatment instrument 10, the treatment instrument 10B is a medical treatment instrument that uses the BLT for performing treatment on the target region. The treatment instrument 10B includes a handle 4A, the sheath 5, the jaw 6, the transducer unit 7, and the ultrasound probe 8. In the following, the handle 4A having a configuration that is different from that described above in the embodiment of FIGS. 1-8 will be described.

The handle 4A is a portion held by an operator by the operator's hand. Furthermore, an operation knob 41A and the operation button 42 are provided on the handle 4A. Furthermore, a switch 48 is provided on the handle 4A. The switch 48 is electrically connected to the controller 31 by a signal line that is not illustrated. The switch 48 outputs a signal to the controller 31 by being pressed.

Furthermore, the operation knob 41A is provided with a projection portion 41a that presses the switch 48 due to a movement of the operation knob 41A.

In this embodiment, the controller 31, the operation knob 41A, and the switch 48 correspond to the liquid supply control mechanism.

The controller 31 controls the adjusting portion 321 (valve) of the liquid source 32 in accordance with pressing down the switch 48 at the projection portion 41a. Specifically, when the controller 31 receives a signal from the switch 48, the controller 31 opens the valve. In the present embodiment, when the operation knob 41A approaches the handle 4A side (see FIG. 13), the switch 48 is pressed and the valve is opened. Namely, when the jaw 6 and the ultrasound probe 8 are in the closed state or the jaw 6 and the ultrasound probe 8 grips the target region, a physiological saline solution is supplied to the end effector and the target region. In contrast, when the operation knob 41A is away from the handle 4A (see FIG. 12), the state in which the switch 48 at the projection portion 41a is pressed is cancelled and the valve is closed.

In the embodiment described above, the switch 48 is pressed by an operation of the operation knob 41A and a supply of the physiological saline solution is controlled. Specifically, when the jaw 6 and the ultrasound probe 8 are in the closed state due to a movement of the operation knob 41A or the jaw 6 and the ultrasound probe 8 grips the target region, a physiological saline solution is supplied to the end effector. According to this embodiment, because the physiological saline solution is supplied to the target region without the operator directly pressing the operation button, it is possible to improve the operability related to the supply of the physiological saline solution to the treatment portion in the treatment instrument.

Furthermore, in the present embodiment described above, similarly to the embodiment of FIGS. 1-8, because the physiological saline solution is supplied to the target region before energy is applied, it is possible to prevent the target region solidified or dried due to the applied energy from being attached to the jaw 6 or the ultrasound probe 8.

Figure 14:
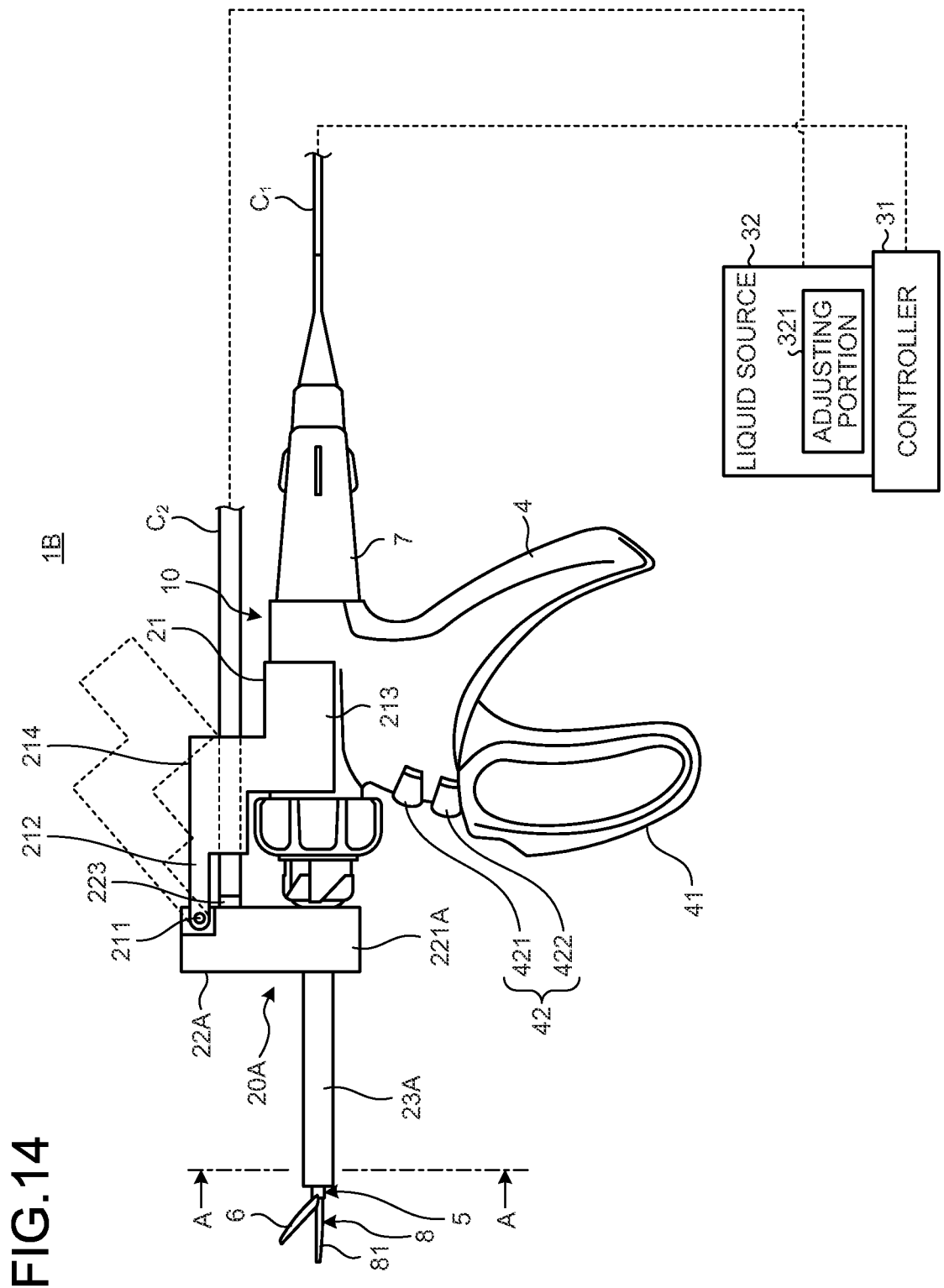
FIG. 14 is a diagram illustrating a treatment device according to an exemplary embodiment of the disclosure.

FIG. 14 is a diagram illustrating a treatment device according to another exemplary embodiment of the disclosure. A treatment device 1B illustrated in the drawing performs treatment on a target region by applying ultrasound energy or high frequency energy to the target region. The treatment device 1B includes the treatment instrument 10, a liquid supply device 20A, the controller 31, and the liquid source 32. The treatment device 1B according to this embodiment has the same configuration as that of the treatment device 1 described above except that the liquid supply device 20 in the treatment device 1 is replaced with the liquid supply device 20A. In the following, the liquid supply device 20A having a different configuration from that described in the above embodiment of FIGS. 1-8 will be described.

The liquid supply device 20A is attached on the outer circumference of the handle 4 and the sheath 5 so as to be freely inserted to and removed from the handle 4 and the sheath 5. The liquid supply device 20A includes the fixing portion 21 that is fixed to the handle 4, a coupling portion 22A that couples the inner portion of the main channel 23 and the inner portion of the liquid supply tube $C_2$ from the liquid source 32, and a main channel 23A that extends along the sheath 5. The fixing portion 21 is pivotally supported by the hinge portion 211 of the coupling portion 22A. Furthermore, an insertion portion 214 that allows the tube $C_2$ to be inserted into the fixing portion 21 is provided in the holding portion 213 of the fixing portion 21. In the following, the coupling portion 22A and the main channel 23A each having a configurations different from that of the above embodiment (FIGS. 1-8) will be described.

The coupling portion 22A includes a fixed adapter 221A. A description will be given with the assumption that the outer shape of the fixed adapter 221A and the rotating adapter 222 is a circular shape; however, an appropriate shape is allowed. The rotating adapter 222 is the same as that described in the above embodiment of FIGS. 1-8.

A connector 223 that is connected to the tube $C_2$ is disposed on the fixed adapter 221A. Furthermore, a through hole (not illustrated) that connects the connector 223 and the main channel 23A is formed in the fixed adapter 221A.

The fixed adapter 221A is coupled to the fixing portion 21. Accordingly, when the fixing portion 216 is fixed to the handle 4, the fixed adapter 221A maintains the positioning state with respect to the handle 4.

The main channel 23A has a tubular shape that covers the sheath 5.

Figure 15:
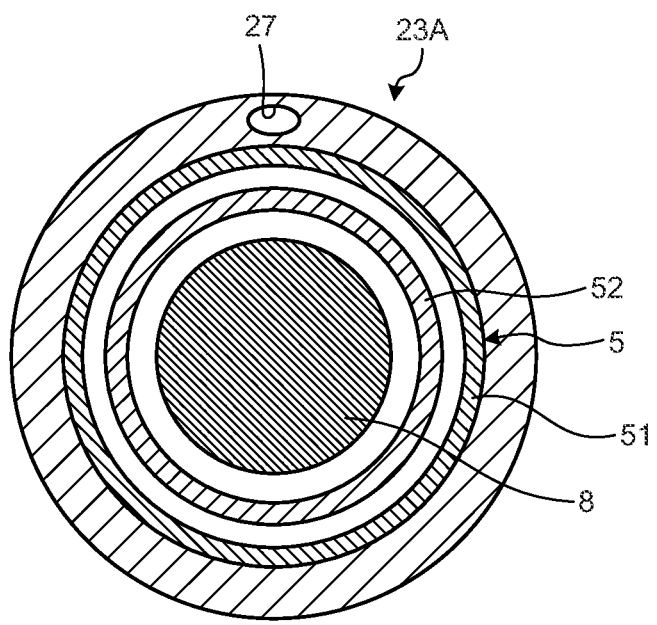
FIG. 15 is a sectional view taken along line A-A of a sheath illustrated in FIG. 14.

FIG. 15 is a sectional view taken along line A-A of the sheath illustrated in FIG. 14. Furthermore, the sheath 5 constituted by an outer sheath 51 and an inner sheath 52 and the ultrasound probe 8 is inserted inside of the inner sheath 52. The inner sheath 52 moves, in conjunction with an operation of the operation knob 41, in the direction orthogonal to the plane of the drawing (for example, the distal end side A1 or the proximal end side A2 in FIG. 1) With respect to the outer sheath 51. The jaw 6 is attached to the distal end of the inner sheath 52 and is opened and closed with respect to the ultrasound probe 8 in conjunction with the movement of an inner sheath 52.

A water supply hole 27 extending in an extending direction of the main channel 23A is provided in the main channel 23A. The physiological saline solution that reaches the main channel 23A via the tube $C_2$ and the fixed adapter 221A is introduced into the water supply hole 27 and is discharged from the distal end of the main channel 23A. Furthermore, the timing at which the physiological saline solution is discharged from the main channel is the same as that described above in the above embodiment of FIGS. 1-8.

In the present embodiment, similarly to the embodiment of FIGS. 1-8, the controller 31 detects a change in impedance between the jaw 6 and the ultrasound probe 8 and controls the adjusting portion 321 (valve) of the liquid source 32 in accordance with the detection result. Furthermore, the embodiment is not limited to this, discharge control of the physiological saline solution may also be performed by the clamp 62 by using the jaw 6A described in the embodiment of FIGS. 9-11, or discharge control of the physiological saline solution may also be performed by an operation of the operation knob 41A by using the configuration described in the embodiment of FIGS. 12 and 13.

Furthermore, in the present embodiment, similarly to the embodiment of FIGS. 1-8, because the physiological saline solution is supplied to the target region before energy is applied, it is possible to prevent the target region solidified or dried due to the applied energy from being attached to the jaw 6 or the ultrasound probe 8.

Figure 16:
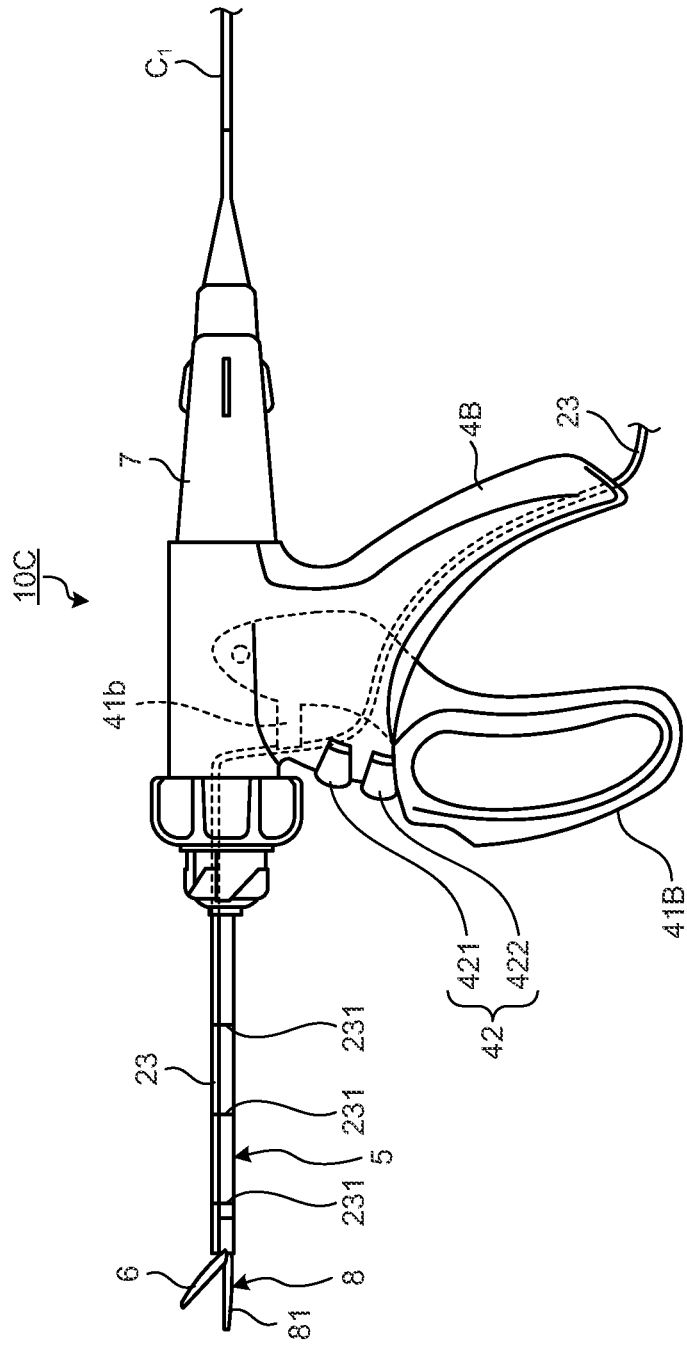
FIG. 16 is a diagram illustrating a treatment instrument in a treatment device according to an exemplary embodiment of the disclosure.
Figure 17:
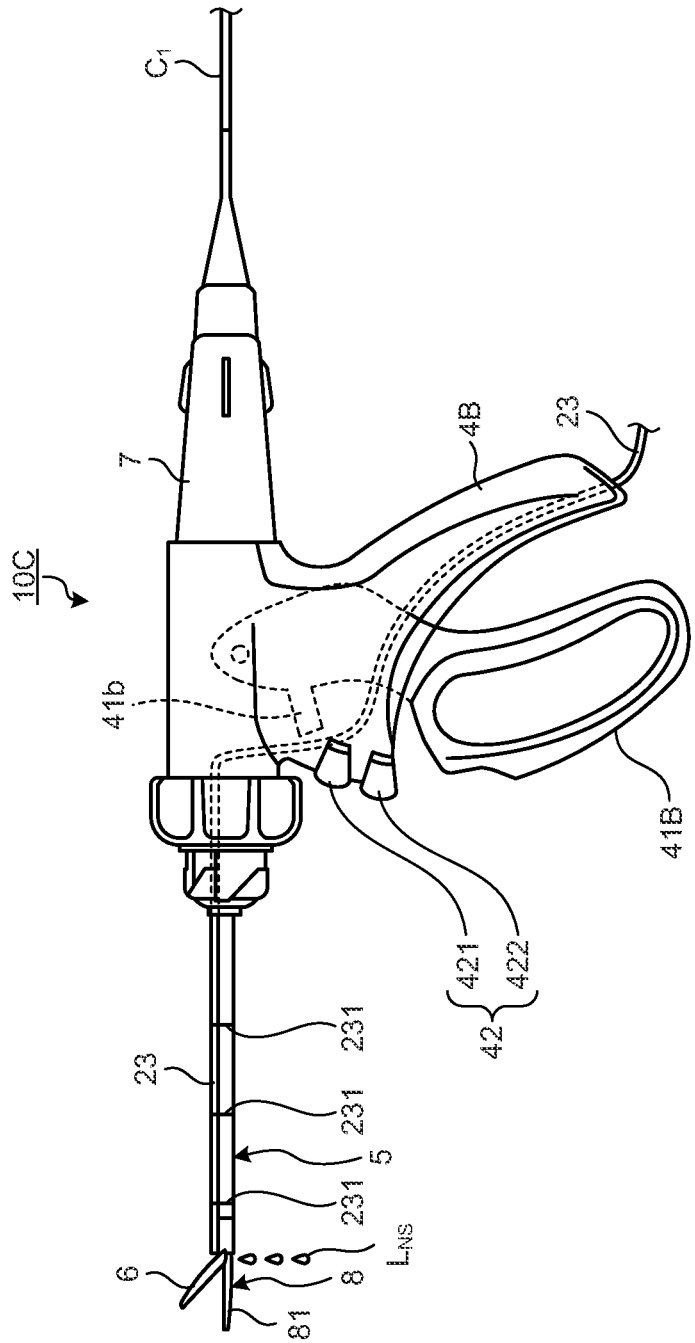
FIG. 17 is a diagram illustrating the treatment instrument in the treatment device according to an exemplary embodiment of the disclosure.

FIG. 16 and FIG. 17 are diagrams each illustrating a treatment instrument in a treatment device according to another exemplary embodiment of the disclosure. The treatment device according to the present embodiment performs treatment on a target region by applying ultrasound energy or high frequency energy to the target region. The treatment device has the same configuration as that described in the embodiment of FIGS. 12 and 13 except that the treatment instrument 10B described above in the embodiment of FIGS. 12 and 13 is replaced with a treatment instrument 10C and the controller 31 is replaced with the controller 31A described in the embodiment of FIGS. 9-11. In the following, the treatment instrument 10C having a different configuration from that described in the embodiment of FIGS. 12 and 13 will be described.

Similarly to the treatment instrument 10, the treatment instrument 10C is a medical treatment instrument that uses the BLT for performing treatment on the target region. The treatment instrument 10C includes a handle 4B, the sheath 5, the jaw 6, the transducer unit 7, and the ultrasound probe 8. In the following, the handle 4B having a configuration different from that described above in the embodiment of FIGS. 1-8 will be described.

The handle 4B is a portion held by an operator by the operator's hand. Furthermore, an operation knob 41B and the operation button 42 are provided on the handle 4B. Furthermore, a projection portion 41b is provided on the operation knob 41B.

The main channel 23 is inserted into the interior of the handle 4B in the treatment instrument 10C. In the interior of the handle 4B, The main channel 23 is fixed to the wall surface on which the transducer unit 7 is connected.

The controller 31A performs control of a supply of a physiological saline solution with respect to the liquid source 32 at a predetermined set flow rate.

In the present embodiment, the controller 31A, the operation knob 41B, and the switch 48 correspond to the liquid supply control mechanism.

In the state in which the operation knob 41B is away from the handle 4B, because the projection portion 41b crushes the main channel 23 (see FIG. 16), the physiological saline solution is not discharged from the main channel 23. In contrast, in a state in which the operation knob 41B approaches the handle 4B, because the contact between the projection portion 41b and the main channel 23 is cancelled (see FIG. 17), a physiological saline solution $L_{NS}$ is discharged from the main channel 23. In the present embodiment, if the operation knob 41B approaches the handle 4B, i.e., if the jaw 6 and the ultrasound probe 8 are in the closed state or if the jaw 6 and the ultrasound probe 8 grasp the target region, the physiological saline solution is supplied to the end effector and the target region.

In the present embodiment described above, the supply of the physiological saline solution is controlled by changing the contact mode between the projection portion 41b and the main channel 23 in accordance with the operation of the operation knob 41B. Specifically, if the jaw 6 and the ultrasound probe 8 are in the closed state due to an operation of the operation knob 41B or if the jaw 6 and the ultrasound probe 8 grip the target region, the physiological saline solution is supplied to the end effector. According to the present embodiment, because the physiological saline solution is supplied to the target region without pressing the operation button, it is possible to improve the operability of a supply of the physiological saline solution to the treatment portion in the treatment instrument.

Furthermore, in the present embodiment described above, similarly to the embodiment of FIGS. 1-8 described above, because the physiological saline solution is supplied to the target region before energy is applied, it is possible to prevent the target region solidified or dried due to the applied energy from being attached to the jaw 6 or the ultrasound probe 8.

Figure 18:
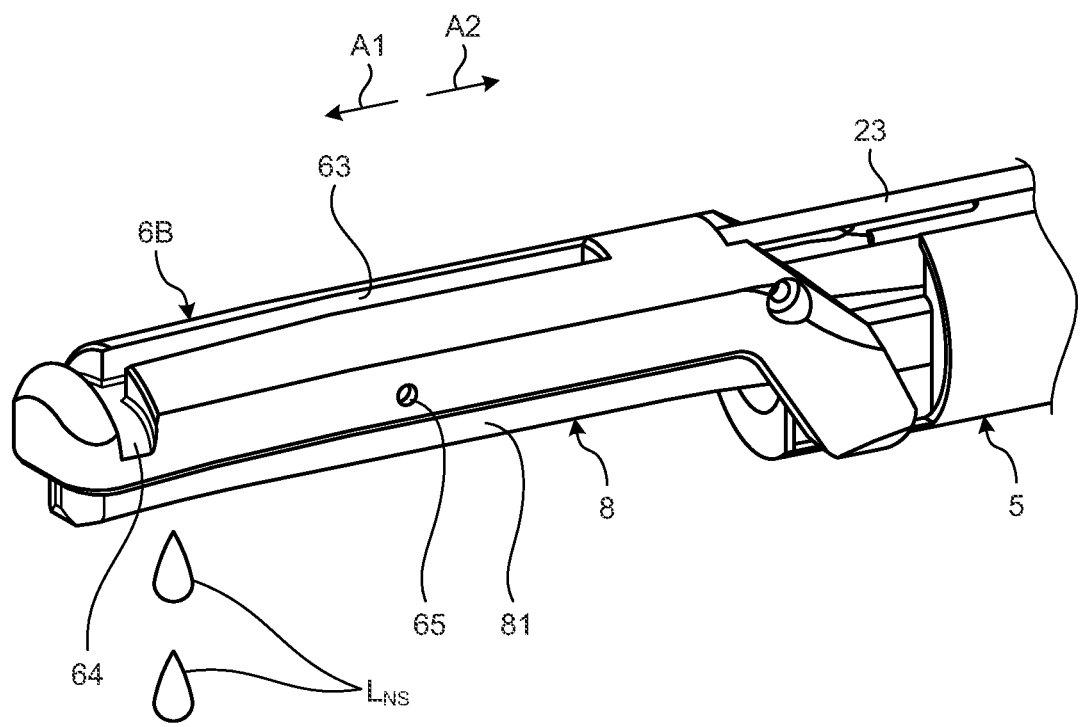
FIG. 18 is a diagram illustrating a distal end portion of a treatment instrument in a treatment device according to an exemplary embodiment of the disclosure.

FIG. 18 is a diagram illustrating a distal end portion of a treatment instrument in the treatment device according to another exemplary embodiment of the disclosure. In the embodiments described above (FIGS. 1-17), a description has been given with the assumption that the physiological saline solution flows by arranging the distal end portion of the main channel 23 on the proximal end side A2 of the jaw 6; however, in the present embodiment, a physiological saline solution flows from the distal end side A1 in a jaw 6B. The treatment device according to the present embodiment performs treatment on a target region by applying ultrasound energy or high frequency energy to the target region. The treatment device has the same configuration as that described in the embodiment of FIGS. 1-8 except that, in the treatment instrument 10 described above in the embodiment of FIGS. 1-8, the jaw 6 is replaced with the jaw 6B. In the following, the jaw 6B having a configuration different from that described in the embodiment of FIGS. 1-8 will be described.

The jaw 6B is attached in a rotatable manner to the end portion of the distal end side A1 of the sheath 5 and grips the target region between the portion of the distal end side A1 of the ultrasound probe 8. Furthermore, an opening and closing mechanism that opens and closes the jaw 6B with respect to the distal end side A1 of the ultrasound probe 8 in accordance with an operation of the operation knob 41 performed by an operator is provided in the interior of the handle 4 and the sheath 5 described above. An end effector is constructed by the jaw 6B and the ultrasound probe 8.

A water supply groove 63 that supplies a physiological saline solution discharged from the main channel 23 to the distal end side A1 of the jaw 6B is formed in the jaw 6B.

The water supply groove 63 extends in the direction of the distal end side A1 from the proximal end portion of the jaw 6B. The distal end of the water supply groove 63 is located at the distal end of the jaw 6B and in which a discharging groove 64 is branched into two. Furthermore, a discharging port 65 is formed at the center portion in the direction of the distal end side A1 of the water supply groove 63. In the water supply groove 63, a physiological saline solution is discharged from the distal end and the center portion of the jaw 6B, and then, the discharged physiological saline solution flows to the end effector and the target region. At this time, similarly to the embodiment of FIGS. 1-8, the opening of the main channel 23 is located on the proximal end side of the jaw 6B. In the present embodiment, a channel is formed by the main channel 23 and the water supply groove 63.

Furthermore, at least one of the discharging groove 64 and the discharging port 65 may be provided in the water supply groove 63.

The physiological saline solution discharged from the main channel 23 flows from the distal end side of the jaw 6B via the water supply groove 63 to the end effector and the target region. Furthermore, the timing at which the physiological saline solution is discharged from the main channel is the same as that described above in the embodiment of FIGS. 1-8. Accordingly, in the present embodiment, similarly to the embodiment of FIGS. 1-8 described above, because the physiological saline solution is supplied to the target region before energy is applied, it is possible to prevent the target region solidified or dried due to the applied energy from being attached to the jaw 6B or the ultrasound probe 8.

The features of the embodiment of FIG. 18 may be combined with any of the other embodiments (e.g., FIGS. 1-17 and 19) disclosed herein. For example, the jaw 6B of FIG. 18 may be combined with the jaw 6A of FIGS. 9-11 including the clamp 62 to open and close the channel 23. For instance, the clamp 62 may include an opening to permit fluid flow therethrough from the channel 23 to the water supply groove 63 when the jaw 6B is in the closed state. Alternatively, the jaw 6B of FIG. 18 may be combined with embodiment of FIGS. 16 and 17 in which the operation knob 41B is designed to open and close the channel 23, or the other embodiments in which the controller 31 controls the adjusting portion 321 to start and stop fluid flow to the channel 23 based on a detected change.

Furthermore, in addition to the embodiment of FIG. 18 described above, for example, it may also be possible to use a configuration in which a physiological saline solution flows from the center portion of the jaw 6 in the direction of the longitudinal axis Ax or a configuration in which a physiological saline solution flows from at least two locations from among the proximal end side, the center portion, and the distal end side may also be used.

In the above, detailed description of the preferred embodiments have been described; however, the disclosure is not limited to only the embodiments described above. The disclosure can include various embodiments or the like that are not described here. In the embodiments described above, the treatment instrument 1 applies a high frequency current and an ultrasound vibration to the biological tissue; however, the configuration is not limited to this. It may also be possible to use a configuration in which one of the ultrasound vibration and the high frequency current is applied or a configuration in which thermal energy is applied, or it may also be possible to use a configuration in which an ultrasound vibration, a high frequency current, and thermal energy are selectively applied. Furthermore, it may also be possible to use a configuration in which only the biological tissue is grasped without applying energy, such as an ultrasound vibration. In a case of configuration in which the treatment instrument only grasps the biological tissue, the pair of grippers acts as a pair of jaws.

Furthermore, in the above embodiments, a description has been given of a case in which a physiological saline solution flows to the end effector; however, water or a medical agent may also be supplied other than the physiological saline solution. Furthermore, in addition to supply a liquid via the tube $C_2$ or the water supply hole 27, it may also be possible to use a configuration in which a liquid is supplied in the interior of the main channels 23 and 23A.

Furthermore, in the above embodiments, a description has been given of a case in which a liquid flows to the end effector; however, the liquid around the target region may also be sucked by the tube $C_2$. In this case, a suction pump is provided instead of the liquid source 32. In a case of this configuration, the suction pump corresponds to the fluid source. Furthermore, it may also be possible to use a configuration in which both of the liquid source 32 and the suction pump are provided and a supply and suction may also be switched.

Figure 19:
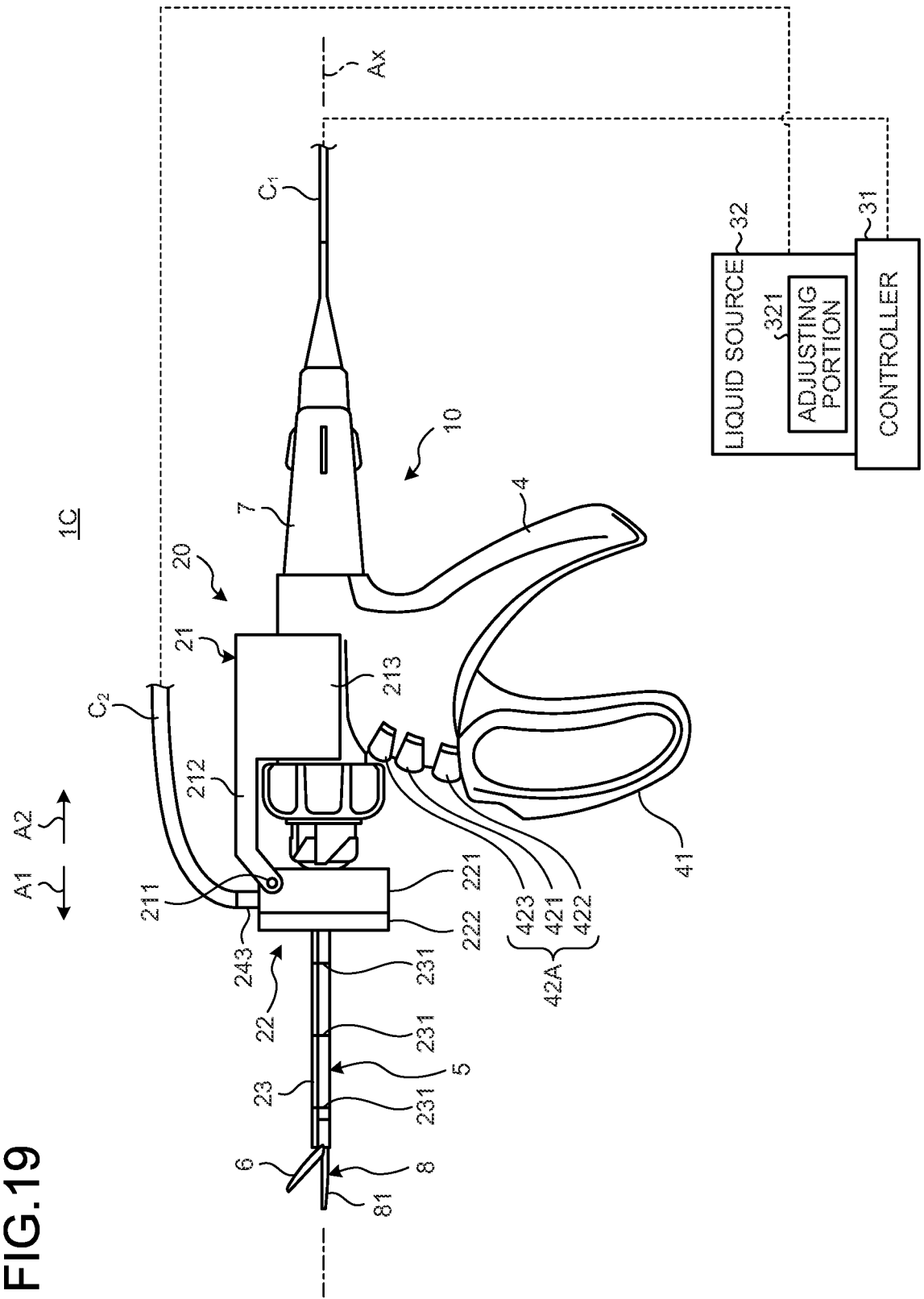
FIG. 19 is a diagram illustrating a treatment device according to an exemplary embodiment of the disclosure.

Furthermore, in the above embodiments, it may also be possible to use a configuration in which, by turning on/off the switch provided in the treatment instrument, a physiological saline solution is not supplied regardless of opening and closing of the jaw 6. FIG. 19 is a diagram illustrating a treatment device according to another embodiment of the disclosure. A treatment device 1C has the same configuration as that described in the embodiment of FIGS. 1-8 except that, in the treatment instrument 10 in the treatment device according to the embodiment described above, the operation button 42 is replaced with an operation button 42A. The operation button 42A includes a switch 423 in addition to the switches 421 and 422. The switch 423 outputs a signal to the controller 31 by being pressed. When the controller 31 receives a signal that is input from the switch 423, the controller 31 stops a supply of a fluid to the end effector regardless of opening and closing of the jaw 6.

INDUSTRIAL APPLICABILITY

As described above, the treatment device according to the disclosure is useful for improving the operability related to a supply of a physiological saline solution to the treatment portion in the treatment instrument.

According to the disclosure, an advantage is provided in that it is possible to improve the operability related to the supply of the physiological saline solution to the treatment portion in the treatment instrument.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
   an end effector that includes a pair of grippers configured to grip a target region;
   a channel that is configured to supply a fluid to the end effector, and is provided with an opening at a position to supply the fluid to the end effector;
   a fluid source configured to supply the fluid to the channel;
   a sheath that extends from a proximal end of the end effector; and
   a clamp that is provided on a first gripper of the pair of grippers, the clamp being arranged on an opposite side of the first gripper from a side facing a second gripper of the pair of grippers, the clamp being configured to:
      close the channel when the end effector is in an open state by crushing the channel against the sheath to block the fluid from flowing through the channel, and
      open the channel when the end effector is in a closed state by releasing the channel to allow the fluid to flow through the opening of the channel.

2. The treatment device according to claim 1, wherein the opening of the channel is located on a proximal end side of the end effector.

3. The treatment device according to claim 2, wherein the end effector is provided with a hole into which the channel is inserted.

4. The treatment device according to claim 2, wherein the end effector includes a water supply groove and the channel is configured to deliver the fluid to the water supply groove.

5. The treatment device according to claim 2, wherein the opening of the channel is arranged in between a distal end of the treatment device and a rotation axis of the pair of grippers.

6. The treatment device according to claim 1, wherein the first gripper of the pair of grippers and the clamp are configured to rotate together with respect to the sheath.

7. A treatment device comprising:
   an end effector that includes a pair of grippers configured to rotate around a rotation axis to grip a target region;
   a sheath that extends from a proximal end of the end effector;
   a channel extending along an outer surface of the sheath, the channel being configured to supply a fluid to the end effector, and including an opening at a position to supply the fluid to the end effector, the opening of the channel being distal of the rotation axis of the pair of grippers;
   a fluid source configured to supply the fluid to the channel; and
   a handle that includes an operation knob that is configured to be operated to:
      open and close the pair of grippers provided in the end effector,
      close the channel when the end effector is in an open state by blocking the fluid from flowing through the channel, and
      open the channel when the end effector is in a closed state by releasing the channel to allow the fluid to flow through the channel,
   wherein the operation knob is configured to be moved: (i) toward the handle to close the pair of grippers and open the channel, and (ii) away from the handle to open the pair of grippers and close the channel.

8. The treatment device according to claim 7, wherein the operation knob includes a projection that is configured to compress the channel to block the fluid from flowing through the channel when the end effector is in the open state.

9. The treatment device according to claim 8, wherein the projection is configured to release the channel to allow the fluid to flow through the channel when the operation knob is operated to close the pair of grippers provided in the end effector.

10. The treatment device according to claim 7, wherein the end effector includes a water supply groove and the channel is configured to deliver the fluid to the water supply groove.

11. The treatment device according to claim 10, wherein the water supply groove extends from a proximal end portion to a distal end portion of a first gripper of the pair of grippers on an opposite side from a second gripper of the pair of grippers.

12. The treatment device according to claim 11, wherein a distal end of the water supply groove branches into two discharging grooves.

13. The treatment device according to claim 11, wherein the first gripper of the pair of grippers further includes a discharging port fluidly connected to the water supply groove at a position in between a proximal end and a distal end of the water supply groove.

* * * * *